US010222329B2

(12) United States Patent
Respini et al.

(10) Patent No.: US 10,222,329 B2
(45) Date of Patent: Mar. 5, 2019

(54) METHOD FOR DETERMINING A SETTLING RATE OF AT LEAST ONE FOULANT IN OIL-BASED FLUIDS

(71) Applicant: BAKER HUGHES INCORPORATED, Houston, TX (US)

(72) Inventors: Marco Respini, Casalmorano (IT); Giuseppe Della Sala, Liverpool (GB)

(73) Assignee: Baker Hughes, a GE company, LLC, Houston, TX (US)

( * ) Notice: Subject to any disclaimer, the term of this patent is extended or adjusted under 35 U.S.C. 154(b) by 303 days.

(21) Appl. No.: 14/862,740

(22) Filed: Sep. 23, 2015

(65) Prior Publication Data

US 2017/0082539 A1 Mar. 23, 2017

(51) Int. Cl.
*G01N 21/59* (2006.01)
*G01N 33/28* (2006.01)
*G01N 15/04* (2006.01)
*C10G 75/00* (2006.01)
*G01N 21/83* (2006.01)
(Continued)

(52) U.S. Cl.
CPC ............ *G01N 21/59* (2013.01); *C10G 75/00* (2013.01); *G01N 15/04* (2013.01); *G01N 21/83* (2013.01); *G01N 33/28* (2013.01); *C10G 2300/206* (2013.01); *G01N 21/359* (2013.01); *G01N 21/3577* (2013.01); *G01N 21/552* (2013.01); *G01N 2021/8416* (2013.01)

(58) Field of Classification Search
CPC ........ G01N 21/59; G01N 33/28; G01N 15/04; G01N 21/83; G01N 2021/8416; G01N 21/552; G01N 21/3577; G01N 21/359; C10G 75/00; C10G 2300/206

USPC .......................................................... 356/70
See application file for complete search history.

(56) References Cited

U.S. PATENT DOCUMENTS 5,863,301 A * 1/1999 Grosso ................... C10L 1/328
137/13
6,467,340 B1 10/2002 Gallagher et al.
(Continued)

OTHER PUBLICATIONS

Marcano et al, "Evaluation of the Chemical Additive Effect on Asphaltene Aggregation in Dead Oils: A Comparative Study between Ultraviolet-Visible and Near-Infrared-Laser Light Scattering Techniques", Jan. 26, 2015, 2015 American Chemical Society, pp. 2813-2822.*

(Continued)

*Primary Examiner* — Hina F Ayub
*Assistant Examiner* — Amanda Merlino
(74) *Attorney, Agent, or Firm* — Mossman, Kumar & Tyler, P.C.

(57) ABSTRACT

A settling rate of at least one foulant in oil-based fluids may be determining a settling rate of an oil-based fluid by stirring the fluid during a turbidimetric flocculation titration, which includes solvent dosing and obtaining transmittance measurements of the oil-based fluid. The method may further include stopping the solvent dosing at the onset of flocculation of the foulant(s), stopping the stirring when at least two or more transmittance measurements are substantially similar, and measuring the transmittance of the oil-based fluid to determine a settling rate of the foulant(s). The settling rate may be proportional to an increase in transmittance or decrease in absorbance after the stirring has stopped.

12 Claims, 3 Drawing Sheets

(51) Int. Cl.
    *G01N 21/3577* (2014.01)
    *G01N 21/359* (2014.01)
    *G01N 21/552* (2014.01)
    *G01N 21/84* (2006.01)

(56) References Cited

U.S. PATENT DOCUMENTS

| | | | |
|---|---|---|---|
| 7,360,403 | B2 | 4/2008 | Jones et al. |
| 9,038,451 | B2 * | 5/2015 | Sandu ............... G01N 21/8507 73/152.02 |
| 2005/0040072 | A1 | 2/2005 | Respini et al. |
| 2008/0099722 | A1 | 5/2008 | Stark et al. |
| 2008/0185316 | A1 | 8/2008 | Respini et al. |
| 2011/0278460 | A1 | 11/2011 | Respini |
| 2013/0341241 | A1 * | 12/2013 | Respini ................. G01N 21/41 208/14 |
| 2015/0102224 | A1 | 4/2015 | Respini |

OTHER PUBLICATIONS

Andersen, Simon Ivar, "Flocculation Onset Titration of Petroleum Asphaltenes," Energy & Fuels 13, No. 2, pp. 315-322 (1999).

* cited by examiner

METHOD FOR DETERMINING A SETTLING RATE OF AT LEAST ONE FOULANT IN OIL-BASED FLUIDS

TECHNICAL FIELD

The present invention relates to measuring the transmittance of an oil-based fluid during solvent dosing and stirring thereof and measuring the transmittance of the oil-based fluid once the solvent dosing and stirring has stopped to determine the settling rate of at least one foulant present in the oil-based fluid where the settling rate is proportional to an increase in transmittance or decrease in absorbance after the stirring has stopped.

BACKGROUND

As world reserves of light, sweet crudes diminish and worldwide consumption of oil increases, refiners seek methods for extracting useful products such as gasoline and fuel oils from heavier crude resources. While not as desirable and easy to process, extensive reserves in the form of "heavy crudes" exist in a number of countries, including Western Canada, Venezuela, Russia, the United States, and elsewhere.

Such heavy oils (even some not so heavy oils) are often difficult to refine because of their viscosity and propensity for being unstable and precipitating solids, such as asphaltenes, coke, coke precursors, etc. upon storage and processing, most notable asphaltenes. Asphaltenes are most commonly defined as that portion of petroleum, which is soluble in xylene and toluene, but insoluble in heptane or pentane. Asphaltenes exist in crude oil as both soluble species and in the form of colloidal dispersions stabilized by other components in the crude oil. Asphaltenes have higher molecular weights and are the more polar fractions of crude oil, and can precipitate upon pressure, temperature, and compositional changes in crude oil resulting from blending or other mechanical or physicochemical processing. Asphaltene precipitation and deposition can cause problems in subterranean reservoirs, upstream production facilities, mid-stream transportation facilities, refineries, and fuel blending operations. In petroleum production facilities, asphaltene precipitation and deposition can occur in near wellbore reservoir regions, wells, flowlines, separators, and other equipment.

When asphaltenes precipitate from crude oil, they can foul equipment and reduce the quality of the products being refined. Other issues associated with heavy crude oil include: high solids; increased amounts of entrained water; and high sulfur content; high total acid number (TAN) and high metals. Asphaltene deposition is a well-known problem affecting all aspects of petroleum production and processing. Crude oils containing high or low levels of asphaltenes can be destabilized while processing causing fouling, formation of sludge, corrosion and all the equipment fixing, cleaning, and cost aggravations associated with these effects.

Additional operational problems observed with heavy crude oil: difficulty in blending crude streams, increased unit upsets, increased pollution, loss of through-put, difficulty with desalting, increased load on wastewater plants, increase in air emissions, and flexibility in plant operations is reduced. All of this leads to an overall increase in operating costs.

Asphaltenes may be present and stable in a crude oil under equilibrium reservoir conditions, but may aggregate or deposit as temperatures, pressures, and overall fluid compositions change as the crude oil is removed from the reservoir during production and/or being further refined. Asphaltenes are typically dark brown to black-colored amorphous solids with complex structures and relatively high molecular weights.

Asphaltene stability can even be disturbed by mixing hydrocarbon-based fluids i.e. such as mixing two types of crude oils together, two types of shale oils together, condensates, and others, of different origins at certain ratios as the chemistry of the hydrocarbon-based fluids from different sources may be incompatible and induce destabilization of the asphaltenes therein. In non-limiting examples, such as during refining or fuel blending, two or more hydrocarbon-based fluids may be mixed together. Sometimes, changes in physical conditions are sufficient to induce destabilization, or even the mixture of different hydrocarbon-based fluids that have incompatible chemistries. Said differently, even if neither oil-based fluid, alone, has destabilized foulants or the hydrocarbon-based fluid would not act as a destabilizing additive by itself, the mixing or the mixture of two or more hydrocarbon-based fluids may further destabilize the foulants present in either hydrocarbon-based fluid.

There are several shortcomings when measuring asphaltene stability to improve foulant stability. Thus, it would be desirable to develop better methods of analyzing the stability of the asphaltenes within crude oils.

SUMMARY

There is provided, in one form, a method for determining a settling rate of at least one foulant in oil-based fluids by stirring an oil-based fluid during a turbidimetric flocculation titration of the oil-based fluid where the turbidimetric flocculation titration includes solvent dosing and obtaining transmittance measurements of the oil-based fluid during the turbidimetric flocculation titration. The method may further include stopping the solvent dosing at the onset of flocculation of the at least one foulant, stopping the stirring when at least two or more transmittance measurements are substantially similar, and measuring the transmittance of the oil-based fluid to determine a settling rate of the at least one foulant. The settling rate may be proportional to an increase in transmittance after the stirring has stopped.

In an alternative non-limiting embodiment, the method may include implementing a change to a process associated with the oil-based fluid based on the settling rate of at least one foulant(s) in an oil-based fluid. The settling rate may be determined by obtaining at least two absorbance measurements after solvent dosing and stirring have stopped during a turbidimetric flocculation titration. The settling rate may correlate to −dA/dt where dA is the change in absorbance measurements over a period of time dt.

DETAILED DESCRIPTION

Figure 1:
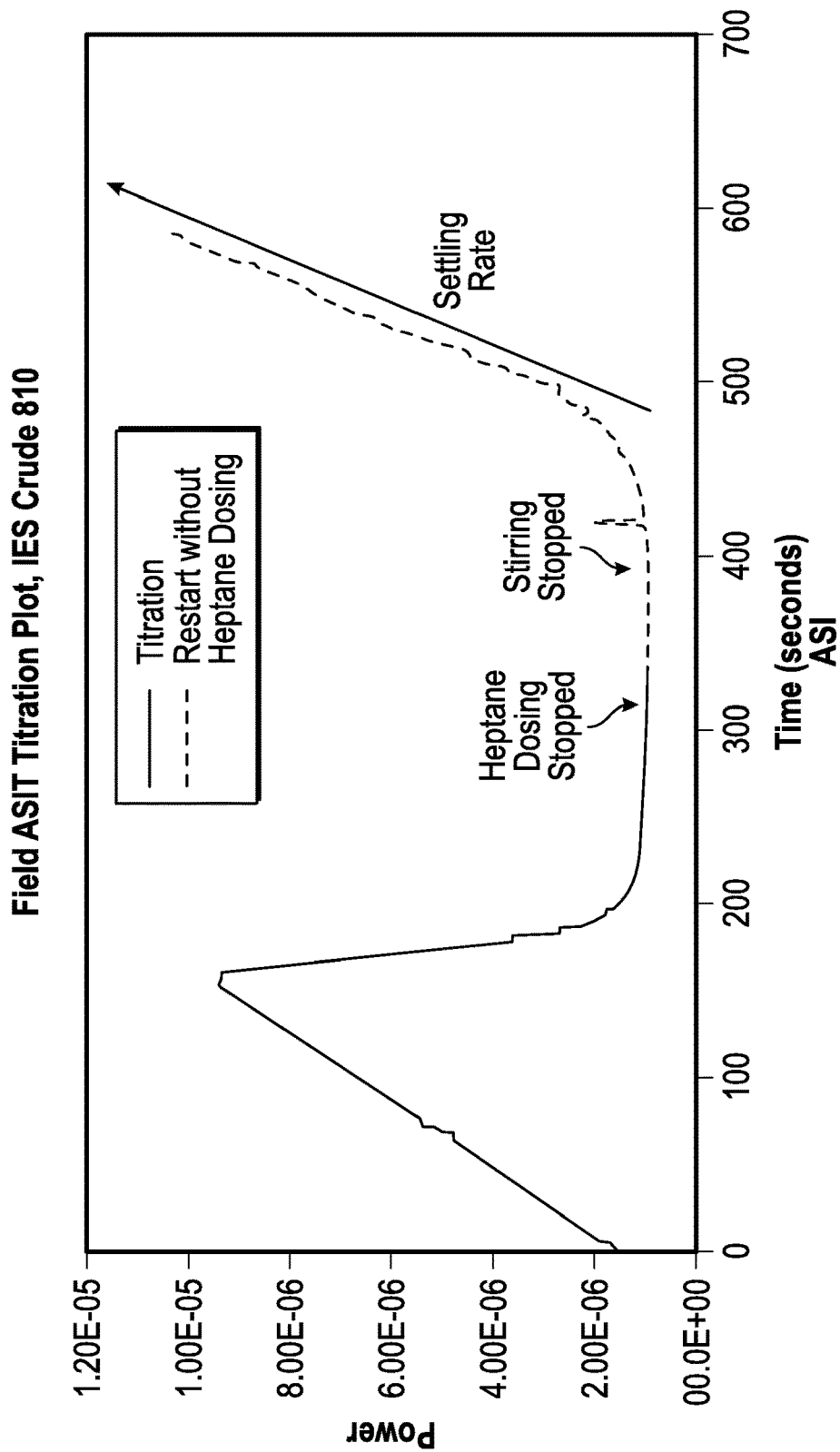
FIGS. 1-2 are graphs illustrating transmittance measurements of an oil-based fluid over a period of time during a turbidimetric flocculation titration.

It has been discovered that the settling rate of at least one foulant within an oil-based fluid may be determined. The method may include stirring an oil-based fluid during a turbidimetric flocculation titration of the oil-based fluid where the turbidimetric flocculation titration method includes solvent dosing and obtaining the transmittance of the oil-based fluid during the turbidimetric flocculation titration. The method of measuring the settling rate may further include stopping the solvent dosing at the onset of flocculation of the foulant(s), and stopping the stirring shortly thereafter when at least two or more transmittance measurements are substantially similar, i.e. the transmittance becomes almost constant by not drastically increasing or decreasing. In a non-limiting embodiment, at least 10 seconds may elapse after the transmittance becomes almost constant before stopping the stirring to ensure the transmittance does not unexpectedly increase or decrease; alternatively, at least 50 seconds may elapse, or at least 100 seconds may elapse in another non-limiting embodiment. The method may include resuspending the foulant(s) by stirring the oil-based fluid after the settling rate has been determined in a non-limiting embodiment.

The transmittance of the oil-based fluid may increase, or the absorbance of the oil-based fluid may decrease, after the solvent dosing and stirring has stopped, and this increase in transmittance or a decrease in absorbance corresponds to the settling rate. In a non-limiting embodiment, the settling rate is proportional to an increase in transmittance after the stirring has stopped. Alternatively, the settling rate is proportional to a decrease in absorbance after the stirring has stopped.

The stirring may be a magnetic stirring in a non-limiting embodiment. The stirring creates a vortex holding the foulant(s) in suspension. When the stirring is stopped, the foulant(s) may settle because of gravity, and the change of measured transmittance and/or absorbance may be used to measure the settling rate.

The settling rate may be used to determine oil-based fluid stability when oil-based fluid is being transported, moved or processed. It would be desirable to avoid destabilization of the oil-based fluid after transportation and storage, and/or processing once precipitation of the foulant(s) and aggregation is formed. A settling rate need only be determined periodically, sometimes as infrequently as once per "batch" of oil-based fluid (e.g. crude oil). Of course, in some embodiments where large batches of oil-based fluids are being transported or stored or blended, it may be desirable to run this test more frequently. Generally speaking though, once the settling rate has been determined, these values do not tend to change absent a substantial change to the conditions and/or quality of the oil-based fluid.

In another non-limiting embodiment, a foulant (e.g. asphaltene) settling rate of a first oil-based fluid may be compared to a foulant (e.g. asphaltene) settling rate of a second oil-based fluid to properly ratio a blend of the first oil-based fluid and second oil-based fluid entering into a storage vessel. In another non-limiting embodiment, the ratio of the first oil-based fluid and second oil-based fluid may allow for better monitoring of homogenization of the contents of the storage vessel. In this non-limiting example, two oil-based fluids are compared; however, comparing settling rates of three or more oil-based fluids may also be performed for purposes of blending the oil-based fluids.

In a non-limiting embodiment, the stirring may occur at a rate ranging from about 200 rpm independently to about 1200 rpm, alternatively, 400 rpm independently to about 1000 rpm, or from about 600 rpm independently to about 800 rpm in another non-limiting embodiment.

If an oil-based fluid has a settling rate within a pre-determined range, then the operator may elect to maintain the process within a refinery. The pre-determined range may be from about 0 independently to about $0.0005 \text{ (s)}^{-1}$. If the settling rate falls outside of the pre-determined range, then the operator may elect to change the process within a refinery.

A change to at least one refinery process may be necessitated pending the results of the settling rate for the foulant(s). Such change(s) may be or include, but is not limited to, adding an additional feed stream to the oil-based fluid to stabilize the oil-based fluid, adding an additive to the oil-based fluid, adding a different demulsifier to the oil-based fluid than any demulsifier already present in the oil-based fluid, changing a temperature of the oil-based fluid, changing a water feed rate of a unit within the refinery process, and combinations thereof. Other non-limiting examples of changes that may occur include changing the oil-based fluids to be blended, changing the oil-based fluid mixing order, etc. In one non-limiting embodiment of the method of the application, the operator may elect to change operating parameters including, but not limited to changing fluid flow velocities, changing unit operating temperatures, changing unit residence times, and the like.

In another non-limiting embodiment, the operator may elect to make changes by mixing at least two feed streams to bring the ratio of the settling rates of the combined stream into the pre-determined range. In some embodiments, the second feed stream may not be crude oil. For example, a refinery may elect to use a lighter feed stock such as gas oil, paraffinic feed, lighter cutter stocks, etc. that could be recovered and recycled.

In yet another non-limiting embodiment, the mixing or blending of oil-based feed streams may be the blending of streams that are often prone to problems. One such is the blending of heavy crude oil and shale oil. Shale oil is paraffinic and is often prone to blending problems.

In combining or blending oil-based feed streams, any method of performing this function may be employed. For example, the oil-based feed streams may be introduced into a tank and agitated. In an alternative embodiment, the oil-based feed streams may be co-injected into a line having static mixers in place. In still another embodiment, both methods may be employed to mix crude oil feed streams to prepare a crude oil feed stream.

When the settling rate is not within the pre-determined range, remedial efforts may be employed to mitigate the instability of the oil-based fluid. At least one such remedial effort may include adding a stabilizing additive to the oil-based fluid and/or changing the dosage rate of a stabilizing additive present in the oil-based fluid. Any additive known to be useful to those of ordinary skill in the art may be employed with the method of the application. For example, in one non-limiting embodiment, the additive may be prepared from a formulation including: a first component selected from the group consisting of (alkoxylated)-(di or tri)-alkyl phenol-aldehyde (amine) resins; α-Olefin-maleic anhydride co-polymers and grafted polymers including half ester/amide and full ester/amide derivatives; and combinations thereof. Such a formulation may also include a second component that may be or include, but is not limited to, polyamines, amidoamines, imidazolines, and combinations thereof.

The additives may alter the stability of the oil-based fluid and thereby alter the settling rate of the oil-based fluid or oil-based fluid blend. Such additives may be employed at a concentration ranging from about 0.025 independently to about 10 wt % of the total oil-based fluid or blend, alternatively from about 0.1 independently to about 5 wt %, or from about 1 independently to about 4 wt % in another non-limiting embodiment.

In a non-limiting embodiment, measuring the transmittance of the oil-based fluid includes the use of a laser light passed through the oil-based fluid. The laser light may have a wavelength ranging from about 800 nm independently to about 2500 nm. Alternatively, the wavelength of light may range from about 1000 nm independently to about 2000 nm, or from about 1300 nm independently to about 1800 nm in another non-limiting embodiment.

Turbidimetry is a process of measuring the loss of intensity of transmitted light due to the scattering effect of particles suspended therein. Light may be passed through a filter creating a light of known wavelength that is then passed through a cuvette containing a solution. The turbidimetric flocculation titration may occur with a turbidimetric method, such as but not limited to turbidimetry, nephelometry, infrared spectroscopy by attenuated total reflectance (ATR), and combinations thereof. In a non-limiting embodiment, the foulant(s) for purposes of measuring the settling rate may include asphaltenes.

Nephelometry uses a nephelometer to measure the concentration of suspended particulates in a liquid or gas colloid by employing a light source and a light detector set to one side (e.g. 90 degrees) of the light source beam. Particle density may be a function of light reflected into the detector from the particles. The reflected light may be dependent upon properties of the particles, such as shape, color, and reflectivity.

Attenuated total reflectance is a sampling technique used in conjunction with infrared spectrometry to examine solid or liquid states of samples without further preparation. ATR uses a property of total internal reflection resulting in an evanescent wave. An infrared light beam may be passed through an ATR crystal to reflect at least once off the internal surface in contact with the sample. The reflection forms the evanescent wave that extends into the sample. The penetration depth into the sample may be determined by the wavelength of light, the angle of incidence and the indices of refraction for the ATR crystal and the medium being probed. The ATR crystal may be made of an optical material with a higher refractive index than the sample being studied.

In a non-limiting embodiment, the turbidimetric flocculation titration method may be an optical method using a coherent light source that allows measuring the transmittance through the sample and relates especially to measuring the onset flocculation of foulant(s) (e.g. asphaltenes) within an oil-based fluid sample. Changes in the sample transmittance (such as foulant aggregation and precipitation) may be induced via temperature and/or via adding a solvent. The transmittance changes versus temperature and/or solvent addition may be measured with high degree of sensitivity and repeatability.

The solvent for the solvent dosing during the turbidimetric flocculation titration may be or include, but is not limited to, cetane, heptane, xylene, toluene, hexane, pentane, methylnaphthalene, a paraffinic solvent having a solubility range of about 6.8 to 7.2 $(cal/cm3)^{1/2}$, and combinations thereof. The three dilution approach may be used where oil-based fluid samples of known amounts may be diluted at three different ratios: 1:1, 1:1.5, 1:2, and so on until foulants (e.g. asphaltenes) begin precipitating from the oil-based fluid sample in a non-limiting embodiment. At each dilution, a refractive index measurement may be taken, and the refractive index measurement may be plotted on the x-axis, and the power value corresponding to the particular refractive index measurement may be plotted on the y-axis.

In a non-limiting embodiment, the oil-based fluid may be heated prior to the turbidimetric flocculation titration to decrease the viscosity of the oil-based fluid. The temperature of the oil-based fluid during the heating thereof may range from about 20 C independently to about 250 C, alternatively from about 50 C independently to about 100 C.

In a non-limiting embodiment, the oil-based fluid may be or include, but is not limited to, crude oil, distillation residua, quench oil, visbreaker H-oil, LC bottoms fluid, and combinations thereof. In another non-limiting embodiment, the oil-based fluid may be or include a blend of at least two oil-based fluids, which may be the same oil-based fluids or different oil-based fluids. For example, the blend may be, but is not limited to, two or more crude oils blended together, or the blend may be two or more distillation residua fluids, etc. Alternatively, the oil-based fluid may include, but is not limited to, a blend of two or more oil-based fluids that are different, such as crude oil and quench oil, distillation residua, and LC bottoms fluid, etc.

Prior to measuring the settling rate, the stability of the foulant(s) present in the oil-based fluid may be measured by taking a first refractive index (RI) measurement with a refractive index probe inserted into the oil-based stream (e.g. a crude oil sample) when the oil-based stream is not diluted with a solvent. The first RI measurement may be used to determine a first functional refractive index $(F_{RI})$ value by using the formula $F_{RI}=(RI^2-1)/(RI^2+2)$ where RI is the first refractive index measurement in this instance. The first $F_{RI}$ value may determine as a first solubility parameter, also known as a solubility blending number (SBn), by using the formula $\delta=52.042F_{RI}+2.904$ (2) where $\delta$ is in units of 0.5 MPa and where a linear correlation between the solubility parameter, $\delta$, and FRI at 20° C. may be established.

This correlation was established based on the one-third rule relating to the function of the refractive index divided by the mass density as a constant equal to ⅓ for all different compounds. This rule was validated on more than 229 crude oils at 20° C. as well as higher temperatures up to 80° C.

U.S. patent application Ser. No. 13/924,089 filed Jun. 22, 2012 discusses RI parameters measured online using a refractive index probe to convert the RI values into a "solubility blending number" (SBn) based on a linear correlation. The linear correlation may be established using any method known in the art, such as, for example, that disclosed in the method published by the New Mexico Petroleum Recovery Research Center as PRRC 01-18. This document, authored by Jianxin Wang and Jill Buckley and having the title: Procedure for Measuring the Onset of Asphaltenes Flocculation.

A second refractive index (RI) measurement may be taken with a refractive index probe inserted into the oil-based stream (e.g. a crude oil sample) during a turbidimetric flocculation titration, i.e. the oil-based fluid undergoes a series of dilutions with a solvent to induce asphaltene precipitation. At the point when oil-based fluid begins precipitating foulants, e.g. asphaltene flocculation, a second RI measurement may be taken to determine a second $F_{RI}$ value and thereby determine a second solubility parameter. The second RI measurement may be used to determine the second $F_{RI}$ value. The second solubility parameter may be an insolubility number (In). Only two RI values are obtained in this non-limiting embodiment; however, any number of RI values may be measured with the RI probe and used for determining the stability of an oil-based fluid or blend.

Further stability determinations of a particular oil-based fluid may obtained based on the ratio of the first solubility parameter to the second solubility parameter. The settling rate and/or solubility parameters may help determine whether a particular oil-based fluid/stream may be transported, blended, stored, refined, and combinations thereof. Since settling rates and/or solubility parameters are rarely alike for two oil-based fluids, the operator of any refinery or pipeline or storage facility may use the settling rate and/or solubility parameters to determine the stability of the oil-based fluid in particular equipment and/or systems. Variables in these systems include, pipe lines and storage facilities, pipe diameter, stream temperature, stream velocity, and the availability and type of agitation or stirring present, if any. For a refining unit, variables influencing the stability of the oil-based fluid may include the ability to heat the process streams and residence time inside of reactors, reformers, cokers and other types of refinery equipment.

The invention will be further described with respect to the following Example, which are not meant to limit the invention, but rather to further illustrate the various embodiments.

EXAMPLE

Now turning to the Figures, FIG. 1 is a graph illustrating transmittance measurements of an oil-based fluid over a period of time during a turbidimetric flocculation titration. The first peak is merely a noisy peak; whereas the second peak is the point of asphaltene flocculation. The solvent dosing (i.e. heptane in this set of Examples) was stopped when the asphaltenes began to precipitate, i.e. at the point the first peak appeared. The stirring was subsequently stopped when the transmittance became almost constant, i.e. not increasing and not decreasing. Here, about 100 seconds elapsed before the stirring was stopped to ensure the transmittance would not unexpectedly increase or decrease. The settling rate may be measured after the second peak by determining the slope of the increased transmittance line.

Figure 2:
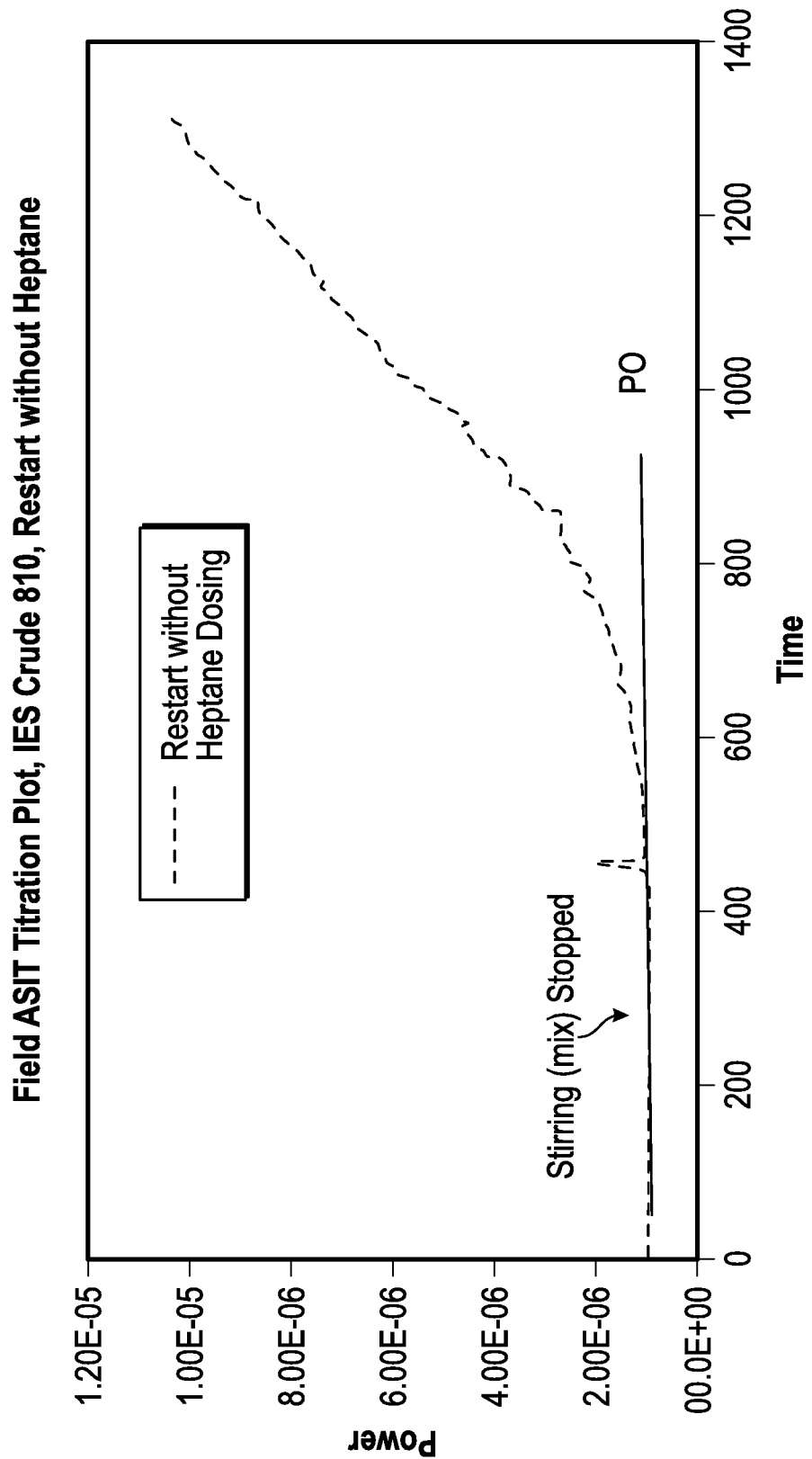

FIG. 2 illustrates a more detailed graph of the settling rate for the same oil-based fluid depicted in FIG. 1 after the heptane dosing has been stopped.

The transmittance may be determined from the graph for the oil-based fluid with the equation:

$$T=P/P0$$

where T is transmittance, P is power at a particular point on the x-axis, P0 is the power of the blank. From the transmittance equation, the absorbance may be determined with the equation:

$$A=-\log(T).$$

The absorbance is proportional to the concentration for diluted solutions using Lambert Beer's Law:

$$A=\varepsilon BC$$

where $\varepsilon$ is an extinction coefficient, B is the cuvette optical path (e.g. 1 cm), and C is the concentration of absorber particles and scatterer particles. The extinction coefficient is given both by absorbance and scattering components:

$$\varepsilon=\varepsilon_{abs}\varepsilon_{scattering}$$

where the concentration of scatterers decrease during settling of the asphaltenic aggregates due to the precipitation of the aspaltenic aggregates from the solution bulk to the cuvette bottom.

Figure 3:
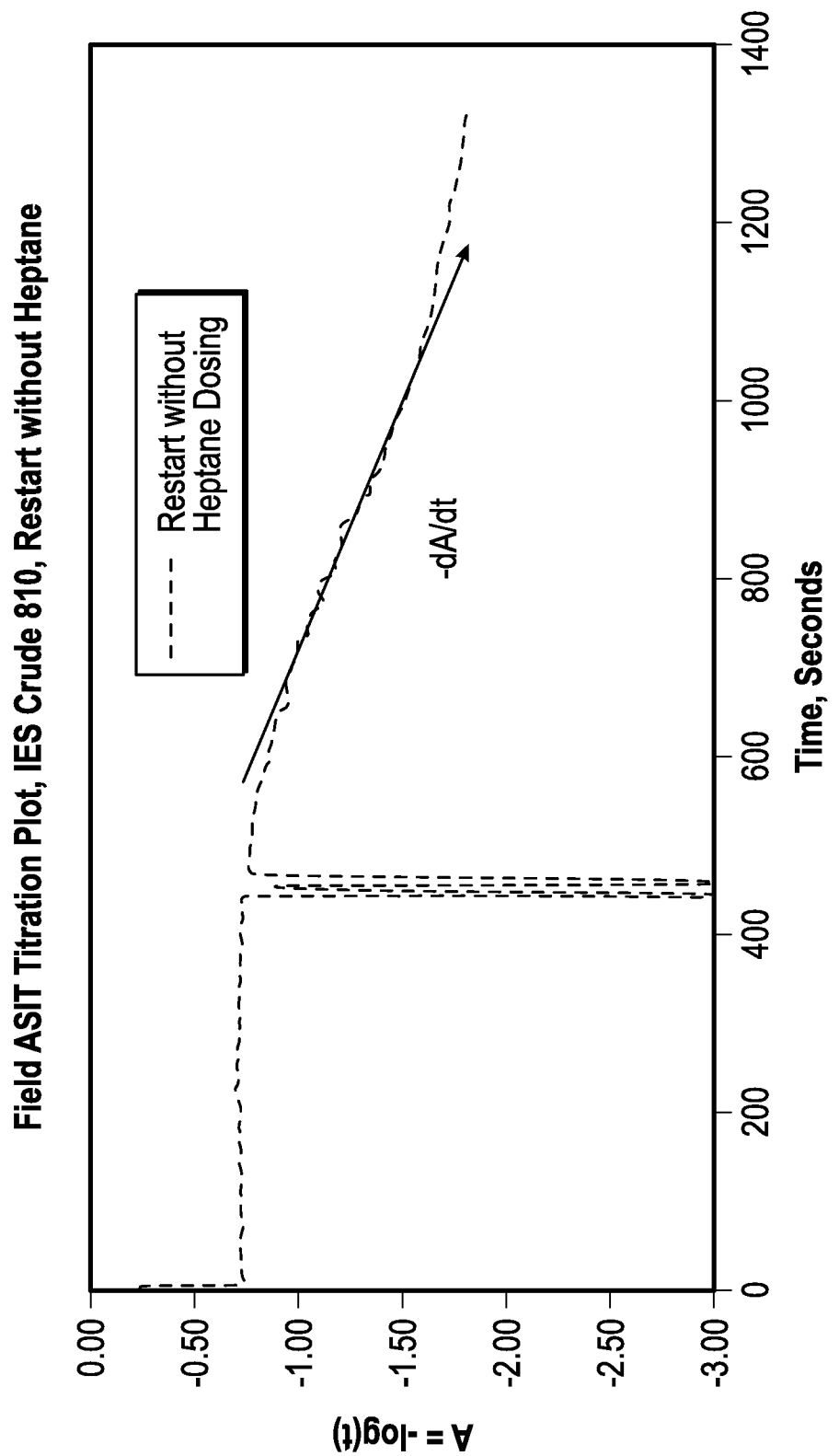
FIG. 3 is a graph illustrating absorbance measurements determined from the transmittance measurements of the oil-based fluid illustrated in FIGS. 1-2.

The settling of the foulant(s) (e.g. asphaltenes) decrease scattering and the absorbance decreases as a consequence as depicted in FIG. 3. The rate of decrease in absorbance is proportional to the rate of decrease of scattering asphaltene aggregates such that:

$$dA/dt=\varepsilon B\ dC/dt.$$

In this way, the absorbance may be used to determine the settling rate where the slope is $-dA/dt$ where dA is the change in absorbance measurements over a change in time dt.

In the foregoing specification, the invention has been described with reference to specific embodiments thereof, and has been described as effective in providing methods for determining a settling rate of at least one foulant in oil-based fluids. However, it will be evident that various modifications and changes can be made thereto without departing from the broader spirit or scope of the invention as set forth in the appended claims. Accordingly, the specification is to be regarded in an illustrative rather than a restrictive sense. For example, specific oil-based fluids, solvents, additives, dispersants, asphaltene inhibitors, additives, tubridimetry methods, laser wavelengths, and the like falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method for determining a settling rate of at least one foulant in oil-based fluids may consist of or consist essentially of implementing a change to a process associated with the oil-based fluid based on the settling rate of at least one foulant(s) in an oil-based fluid; the settling rate may be determined by obtaining at least two absorbance measurements after solvent dosing and stirring have stopped during a turbidimetric flocculation titration; the settling rate correlates to $-dA/dt$ where dA is the change in absorbance measurements over a period of time dt.

The words "comprising" and "comprises" as used throughout the claims, are to be interpreted to mean "including but not limited to" and "includes but not limited to", respectively.

What is claimed is:

1. A method for determining a settling rate of at least one foulant in oil-based fluids comprising:
   stirring an oil-based fluid during a turbidimetric flocculation titration of the oil-based fluid; wherein the turbidimetric flocculation titration comprises solvent dosing and obtaining transmittance measurements of the oil-based fluid during the turbidimetric flocculation titration;
   stopping the solvent dosing;
   stopping the stirring 10 to 100 seconds after a time when at least two or more transmittance measurements are substantially similar;
   measuring the transmittance of the oil-based fluid to determine a settling rate of the at least one foulant; wherein the settling rate is proportional to an increase in transmittance after the stirring has stopped; and
   comparing the at least one foulant settling rate of a first oil-based fluid determined using the foregoing steps to the at least one foulant settling rate of a second oil-based fluid determined using the foregoing steps to create a stable blend of the first oil-based fluid and second oil-based fluid.

2. The method of claim 1, wherein the oil-based fluid is selected from the group consisting of crude oil, distillation residua, quench oil, visbreaker H-oil, LC bottoms fluid, and combinations thereof.

3. The method of claim 1, further comprising resuspending the at least one foulant by stirring the oil-based fluid at a rate ranging from about 200 rpm to about 1200 rpm.

4. The method of claim 1, wherein the measuring the transmittance of the oil-based fluid comprises passing a laser light through the oil-based fluid; and wherein the laser light has a wavelength ranging from about 800 nm to about 2500 nm.

5. The method of claim 1, wherein the turbidimetric flocculation titration occurs with a turbidimetric method selected from the group consisting of turbidimetry, nephelometry, infrared spectroscopy by attenuated total reflectance (ATR), and combinations thereof.

6. The method of claim 1, further comprising implementing a change to a process associated with the oil-based fluid.

7. The method of claim 6, wherein implementing a change to the process is selected from the group consisting of:
adding an additional feed stream to the oil-based fluid to stabilize the oil-based fluid;
adding an additive to the oil-based fluid;
adding a different demulsifier to the oil-based fluid than any demulsifier already present in the oil-based fluid;
changing a temperature of the oil-based fluid;
changing a water feed rate of a unit within the refinery process;
and combinations thereof.

8. The method of claim 1, wherein the solvent dosing comprises a solvent selected from the group consisting of cetane, heptane, xylene, toluene, hexane, pentane, methylnaphthalene, a paraffinic solvent having a solubility range of about 6.8 to 7.2 $(cal/cm^3)^{1/2}$, and combinations thereof.

9. The method of claim 1, wherein the at least one foulant is an asphaltene.

10. The method of claim 1, wherein the transmittance measurements are converted into absorbance measurements, and wherein the settling rate is proportional to a decrease in transmittance after the stirring has stopped.

11. The method of claim 10, wherein the settling rate correlates to $-dA/dt$ where dA is the change in absorbance measurements over a period of time dt.

12. A method for determining a settling rate of at least one foulant in oil-based fluids comprising:
stirring an oil-based fluid during a turbidimetric flocculation titration of the oil-based fluid; wherein the turbidimetric flocculation titration comprises solvent dosing and obtaining transmittance measurements of the oil-based fluid during the turbidimetric flocculation titration;
stopping the solvent dosing;
stopping the stirring 10 to 100 seconds after a time when at least two or more transmittance measurements are substantially similar;
measuring the transmittance of the oil-based fluid to determine a settling rate of the at least one foulant; wherein the settling rate is proportional to an increase in transmittance after the stirring has stopped; and
comparing the at least one foulant settling rate of a first oil-based fluid determined using the foregoing steps to the at least one foulant settling rate of a second oil-based fluid determined using the foregoing steps to bring a setting rate of a blend of the first oil-based fluid and second oil-based fluid into a pre-determined range from about 0 $(s)^{-1}$ to about 0.0005 $(s)^{-1}$.

* * * * *